US007718398B2

(12) United States Patent
Suckow

(10) Patent No.: US 7,718,398 B2
(45) Date of Patent: May 18, 2010

(54) PROMOTERS HAVING A MODIFIED TRANSCRIPTION EFFICIENCY AND DERIVED FROM METHYLTROPHIC YEAST

(75) Inventor: Manfred Suckow, Düsseldorf (DE)

(73) Assignee: Rhein Biotech Gesellschaft fur Neue Biotechnologische Prozesse und Produkte mbH, Dusseldorf (DE)

( * ) Notice: Subject to any disclaimer, the term of this patent is extended or adjusted under 35 U.S.C. 154(b) by 785 days.

(21) Appl. No.: 10/513,836

(22) PCT Filed: May 8, 2003

(86) PCT No.: PCT/EP03/04844

§ 371 (c)(1),
(2), (4) Date: Sep. 12, 2005

(87) PCT Pub. No.: WO03/095653

PCT Pub. Date: Nov. 20, 2003

(65) Prior Publication Data

US 2006/0089492 A1 Apr. 27, 2006

(30) Foreign Application Priority Data

May 10, 2002 (DE) ............................... 102 20 894

(51) Int. Cl.
*C12P 21/02* (2006.01)
(52) U.S. Cl. .................. 435/69.1; 435/91.4; 435/320.1; 435/254.22; 435/254.23; 536/24.1
(58) Field of Classification Search ........................ None
See application file for complete search history.

(56) References Cited

OTHER PUBLICATIONS

Goedecke et al., "Identification of sequences responsible for transcriptional regulation of the strongly expressed methanol oxidase-encoding gene in Hansenula polymorpha," Gene, 139, Elsevier Science B.V. 1994, pp. 35-42, XP-002226643.
Pereira et al., "Conserved regulation of the Hansenula polymorpha MOX promoter in Saccharomyces cerevisiae reveals insights in the transcriptional activation by Adr1p," European Journal of Biochemistry, Bd. 238, 1996, pp. 181-191, XP-001154636.
Suckow, Manfred et al., "The Activation Specificities of Wild-type and Mutant Gcn$p in Vivo can be Different from the DNA Binding Specificities of the Corresponding bZip Peptides in Vitro," Journal of Molecular Biology, London, GB, Bd. 276, 1998, pp. 887-902, XP002189244.
Amuel, Carsten et al., "Analysis of Head Shock Promoters in Hansenula Polymorpha: the TPS1 Promoter, A Novel Element for Heterologous Gene Expression," Biotechnology and Bioprocess Engineering (2000), 5(4), pp. 247-252, XP001154638.
Phongdara, A. et al., "Cloning and characterization of the gene encoding a repressible acid phosphatase (PH01) from the methylotrophic yeast Hansenula polymorpha", Applied Microbiology and Biotechnology, Bd. 50, No. 1, Jul. 1998, pp. 77-84, XP002253409.
Van Dijk, Ralf et al., "The methylotrophic yeast Hansenula polymorpha: a versatile cell factory", Enzyme and Microbial Technology, Bd. 26, No. 9-10, Jun. 2000, pp. 793-800, XP000994959.
Cox, H. et al., "Constitutive expression of recombinant proteins in the methylotrophic yeast Hansenula polymorpha using the PMA1 promoter", Yeast, Chichester, Sussex, GB, Bd. 16, No. 13, Sep. 30, 2000, pp. 1191-1203, XP002226641.
Gellissen, Gerd et al., "Application of yeasts in gene expression studies: a comparison of Saccharomyces cerevisiae, Hansenula polymorpha and Kluyveromyces lactis: A review", Gene: An International Journal on Genes and Genomes, Elsevier Science Publishers, Barking, GB, Bd. 190, Jr. 1, 1997, pp. 87-97, XP002164545.
International Search Report, dated Sep. 23, 2003.
Aki, T., et al., "Identification and Characterization of Positive Regulatory Elements in the Human Glyceraldehyde 3-Phosphate Dehydrogenase Gene Promoter," *J. Biochem*, 1997, pp. 271-278, vol. 122, No. 2.
Bogdanova, A.I. et al., "Plasmid Instability in Methylotrophic Yeast Hansenula polymorpha: The Capture of Chromosomal DNA Fragments by Replicative Plasmids," *Molecular Biology*, 2000, pp. 29-32, vol. 34, No. 1.
Garcia-Gimeno, M. and K. Struhl, "Aca1 and Aca 2, ATF/CREB Activators in *Saccharomyces cerevisiae*, Are Important for Carbon Source Utilization but Not the Response to Stress," *Molecular and Cellular Biology*, Jun. 2000, pp. 4340-4349, vol. 20, No. 12, American Society for Microbiology.
Sellers, J.W., et al., "Mutations that Define the Optimal Half-Site for Binding Yeast GCN4 Activator Protein and Identify an ATF/CREB-Like Repressor That Recognizes Similar DNA Sites," *Molecular and Cellular Biology*, Oct. 1990, pp. 5077-5086, vol. 10, No. 10, American Society for Microbiology.
Vincent, A.C. and K. Struhl, "ACR1, a Yeast ATF/CREB Repressor," *Molecular and Cellular Biology*, Dec. 1992, pp. 5394-5405, vol. 12, No. 12, American Society for Microbiology.

*Primary Examiner*—James S Ketter
(74) *Attorney, Agent, or Firm*—Alston & Bird LLP

(57) ABSTRACT

The present invention relates to a deoxyribonucleic acid (DNA) comprising at least one promoter sequence, which is derived from a wild-type promoter of a methyltrophic yeast, whose transcription efficiency is modulated in comparison to the efficiency of the wild-type promoter by inserting or modifying a DNA binding site. The invention also relates to host cells, expression vectors, kits and methods for producing proteins while using the inventive DNA, as well as to different uses of the same and to a method for producing expression vectors.

17 Claims, 9 Drawing Sheets

Figure 4b

ACTGGTGTCCGCCAATAAGAGAGCCGGCAGGCACGGAGTCTACATCAAGCTGTCTCCGATACACTCGACTACCATCCGGGTCTCTCAGAGAGGGAAT
                        -100                                                              -50

GGCACTATAAATACCGCCTCCTGCGCTCTCTGCTTCATCGGG
                                    -6

Figure 5b

```
-600
CCTTGATCCATTCTATGAGGCCATCTCGAGTGCCTACTCCACTCTGTAGCGACTGGACATCTCGAGACTGGGCTTGCTGTGCTGGAT
          -550
-500
GCACCAATTAATTGTTGCCGCATGCATCCTTGCACCGCAAGTTTTAAAACCCACTCGCNTAGCCCTGTCGCCGTAAAACTTGTGAATNTGGCAACTGAGGG
          -450
                            AC1          -350
-400
GGTTCTGCAGCCGCAACCGAACTTTTGCTTCGAGGACGCAGCTGGA|TGGTGTCATG|GAGGCTCTCTGTTTGCTGGGGTAGCCTACAACGTGACCTTGCCT
-300
AACCGGAACGGGCGCTACCCACTGCTTCTGTGCCTGCTACCAGAAATCACCAGAGGGCCGATGTGGCAACTGGTGTGGTGTCGGACAGGCTG
          -250
-200
TTTCTCCACAGTGCAAATGCGGGTGAACGGCCAGAAAGTAAATTCTTATGCTACCGTGCAGCGACTCCGACATCCCCAGTTTTGCCTACTGATCAC
          -150
-100
AGATGGGGTCAGCGCTGCCGCTAAGTGTACCCAACCGTCCCCACACGGTCCATCTATAAATACTGCTGCCAGTGCACGGTGGTGACATCAATCTAAAGTA
          -50
-6
CAAAAACG
```

Figure 6

```
                    .         .         .         .         .         .
GATGTCAAAATGGGGGATCACAAAAGTACACTCACGAGGAAAATCAAAACATACGAAACATGATCGATTTGAGAAGAT
-550                                                                      -500

.         .         .         .         .         .
TCCTCAATGATTTCGTCATATATAGGTATCTGAGGTATTTATGGACCGATTCGTAATAACATCATATACATCGCGCTTTGTCCCTGTCCCAGAGATTC
      AC5                                                Y1
     -450                                        -400

.         .         .         .         .         .
GATGAAAAAGCGAATTTTATTCTAATATTTGAAGCATGCAAACATGGGGCAGTTGATTGTGTGAGGTAAATATCATGAATGCACCCATCAAATG
                                                                              C2
-350                                    -300

.         .         .         .         .         .
CAGCAAGAGATATTGACCAATCCTATAATAGAAATCAGACTTACCACACAAATAGATTGTGATGAGATATTATGAATCTCCAGATGAATCCGAAAGCTAT
         C1                                              AC4         AC3         AC2
       -250                                      -200

.         .         .         .         .         .
GAAGCCTCTTGAAACTTTCATGGTGAGATATATTTCGAAATTCCACGACTTCTAAAACGCAATTATTGAAGATATAAAGGAAAAATAATATTTCCAT
              AC1                                                              
        -150                                     -100

.         .         .         .         .
ATAGCAAGCAAATCAAGCTGCACTCCCTCATCCTTAAAAACTAATAAATCTTACCCATTGATACCAG
-50                                                              -6
```

|  |  | Center of symmetry ↓ |  |
|---|---|---|---|
| AP1-Sequence | 5' ATGA | C    TCAT 3' | Yeast S. cerevisiae |
| ATF/CREB-Sequence | 5' ATGAC | * G TCAT 3' | Yeast. cerevsiae/mammal |
| YAP-Sequence | 5' ATTAC | * G TAAT 3' | Yeast S. cerevisiae |
| C/EBP-Sequence | 5' ATTGC | * G CAAT 3' | Mammal |
| G-Box | 5' GCCA C | * G TGGC 3' | Plant |

US 7,718,398 B2

PROMOTERS HAVING A MODIFIED TRANSCRIPTION EFFICIENCY AND DERIVED FROM METHYLTROPHIC YEAST

CROSS-REFERENCE TO RELATED APPLICATIONS

This is a U.S. national phase application under U.S.C. §371 International Patent Application No. PCT/EP03/04844, filed May 8, 2003, which claims priority to German Patent Application No. 102 20 894.8, filed May 10, 2002, each of which is hereby incorporated by reference in its entirety.

BACKGROUND OF THE INVENTION

The present invention concerns a deoxyribonucleic acid (DNA) comprising at least one promoter sequence, which is derived from a wild type promoter of a methylotrophic yeast, whose transcription efficiency is modulated compared to the efficiency of the wild type promoter. Further, the present invention concerns host cells, expression vectors, kits and processes for the production of proteins with the use of the DNA according to the invention and various applications thereof and a process for the production of expression vectors.

Because of their capability for mammal-like co- and post-translational modification of proteins, fungi and in particular yeasts are attractive systems for the production of recombinant proteins. For the production of recombinant proteins, the coding sequence of a gene for a protein of interest is often expressed under the control of a suitable heterologous promoter. The inducible promoters from methylotrophic yeasts have proved especially advantageous here.

Methylotrophic yeasts include for example the genera *Candida, Hansenula, Pichia* and *Torulopsis*. Their promoters are characterised by unusually strong transcription induction and good and simple controllability. Particularly advantageous promoters are the promoters responsible in vivo for the regulation of the methanol metabolism. Methylotrophic yeasts catalyse the oxidation of methanol to carbon dioxide via the intermediate stages of formaldehyde and formate, these reactions being catalysed respectively by an alcohol or methanol oxidase (Aoxp or Moxp), a formaldehyde dehydrogenase (Fmdp) and a formate dehydrogenase (Fmdhp). The hydrogen peroxide arising in the first step is degraded by catalase. The C1 compound is assimilated via the transketolase reaction of xylulose-5(P) with formaldehyde. This reaction is catalysed by dihydroxyacetone synthase (Dhasp). The enzymes Aoxp or Moxp, Fmdhp and Dhasp expressed under the control of the AOX or MOX, FMD and DHAS promoters represent up to 40% of the total cell protein in methanol-induced cells. These promoters are thus also described in specialist circles as superpromoters. Most of the promoters for the said genes are repressible with glucose and are therefore very controllable individually.

A further very strong promoter from methylotrophic yeasts is the TPS1 promoter, which controls the expression of the trehalose-6-phosphate synthase gene and is heat-inducible. Tps1p catalyses the conversion of glucose-6-phosphate (GLU6P) and UDP-glucose (UDPG) to trehalose-6-phosphate and UDP. During a one-hour thermal shock from 27° C. to 40° C., treated yeast cells accumulate trehalose and in this way build up increased heat tolerance.

In addition, methylotrophic yeasts have unusually strong constitutive promoters. Two of these very strong constitutive promoters are GAPDH (glyceraldehyde phosphate dehydrogenase) and PMA1 (plasma membrane-bound $H^+$-ATPase 1).

In the recombinant preparation of heterologous proteins, both the activity of the promoter sequence, its regulation and also its integration into the genome of a suitable host cell determine the economic viability and efficiency of the process. In general, especially high transcription activity is desirable. In many cases, however, excessively high transcription activity can lead to the host cell being damaged or dying, before all heterologous gene products of the co- and post-translational modification necessary for the activity could be introduced. In particular, the quantity of toxic proteins must be controlled in such a way that the toxic action is minimised until the optimal yield of transcribed and post-translationally modified proteins. Such control is also difficult to effect with the known promoters inducible with methanol.

BRIEF DESCRIPTION OF THE DRAWINGS

The figures and examples illustrate the invention. The invention is illustrated in more detail below with reference to the figures, which show the following.

Admittedly the value for the FMD id1 promoter after glycerine induction is relatively low both with lacZ and also with phytase as reporter gene, however it is very high in absolute terms (compared to the wt FMD promoter) and moreover is about as high as under glucose conditions. This indicates that FMD id1 is a constitutive promoter with regard to the carbon sources glycerine and glucose. On glucose, FMD id1-4 shows similar values to those for the wt FMD Promoter, however on glycerine it shows markedly higher values. Hence both FMD id1 and also FMD id1-4 show modified regulation and strength compared to the wt FMD promoter.

Figure 2:
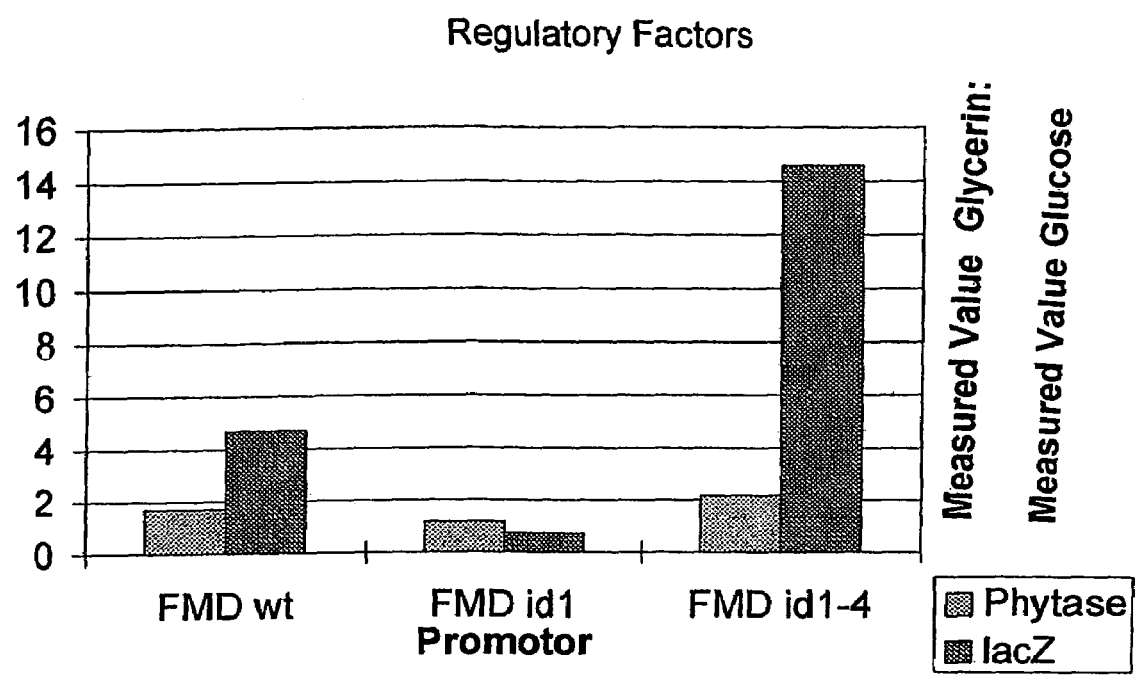

FIG. 2 shows the regulation factors (the quotient of the measured activity values on glycerine and glucose) of the different FMD promoter variants id1 and id1-4 with lacZ (dark grey) or phytase (light grey) as reporter gene compared to the regulation factor of the wild type FMD promoter (FMD wt). A quotient of 1 means that the promoter is constitutive with regard to the carbon sources studied. Values >1 indicate the extent of glycerine derepression. Thus, compared with the wt FMD promoter, the FMD id1 promoter is constitutive, while the FMD id1-4 promoter is more strongly derepressible.

Figure 3:
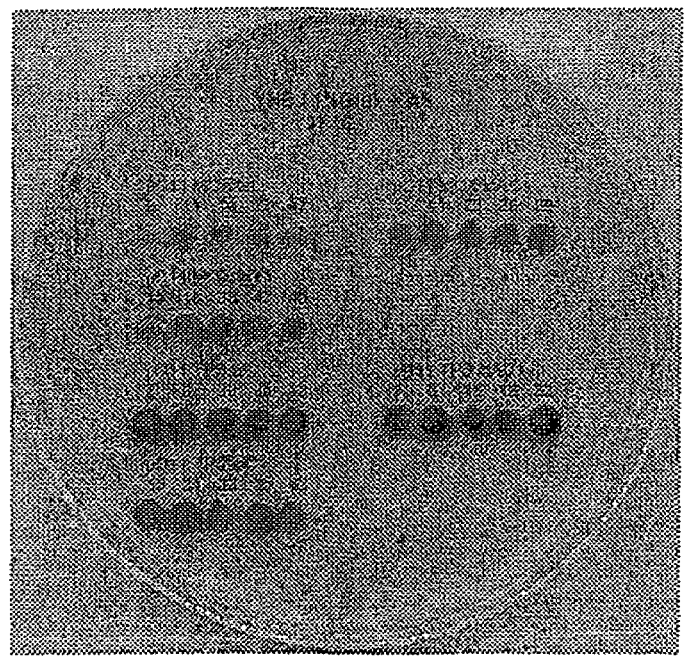

FIG. 3 shows an X-Gal overlay test with strains which had previously been grown at 37° C. on YNB/glucose plates. Both with the MOX plasmid pC11 MOX idAC1 and also with the TPS1 promoter, it was found that the palindromisation of the first (nearest to the TATA box) ATF/CREB sequence-like motif under the tested condition resulted in a visible increase in the promoter activity, compared with the respective wild type promoter (plasmid pC11 MOX wt, plasmid pC11 TPS wt).

MOX Promoter:

Plasmid pC11 MOX idAC1: natural (cryptic) AC1 sequence (atggtgtcat) (SEQ ID NO: 11) idealised by two exchanges to atgacgtcat (SEQ ID NO: 27) (ATF/CREB binding site). The altered bases are underlined (also in the following examples).

Plasmid pC11 MOX idY1: natural (cryptic) Y1 sequence (cgaatgtaat) (SEQ ID NO: 13) idealised by four exchanges to attacgtaat (SEQ ID NO: 28) (YAP binding site).

TPS1 Promoter:

Plasmid pC11 TPS idAC1: natural (cryptic) AC1 sequence (atggtgagat) (SEQ ID NO: 16) idealised by four exchanges to atgacgtcat (SEQ ID NO: 29) (ATF/CREB binding site).

Plasmid pC11 TPS idC1: natural (cryptic) C1-Sequenz (attgaccaat) (SEQ ID NO: 20) idealised by two exchanges to attgcgcaat (SEQ ID NO: 30) (C/EBP binding site)]

FIGS. 4 to 6: In FIGS. 4 to 6, the TATA box and individual cryptic binding sites are represented as follows.

Double underlined: presumed TATA BOX.

Framed with continuous line: possible cryptic ATF/CREB binding sites for bZip proteins.

Framed with broken line: possible cryptic YAP binding sites for bZip proteins.

(AC=cryptic ATF/CREB binding site; Y=cryptic YAP binding site; C=cryptic C/EBP binding site). —The bases with homology to the consensus sequence are underlined.

The numbering is based on the translation start. All the sequences quoted end with guanine. This guanine is in each case the first base of an EcoR1 cleavage site gaattc. Each start codon follows directly thereafter. Hence, based on the atg, the said guanine has the number (−6).

Figure 4A:
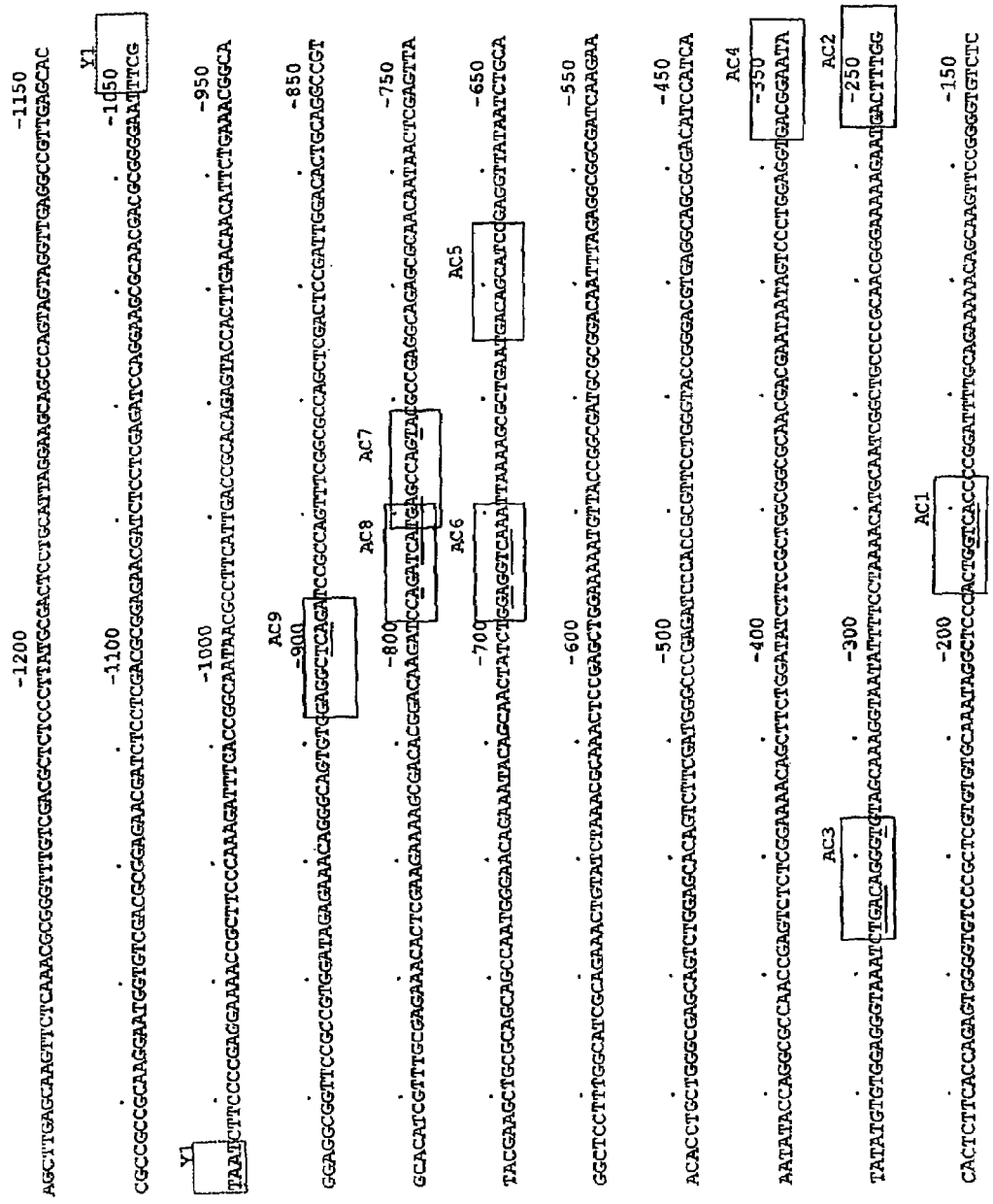

FIGS. 4a and 4b shows the sequence of the wild type FMD promoter with presumed TATA box and possible cryptic binding sites for bZip proteins used in the examples (SEQ ID NO: 24).

The sites 1 to 4 framed with continuous lines, which are all cryptic variants of the ATF/CREB sequence, were modified. The idealised variants were designated as id1 to id4.

AC: Cryptic ATF/CREB sequence.

id# The cryptic ATF/CREB sequence of each respective number was converted into an ideal ATF/CREB sequence.

Figure 5A:
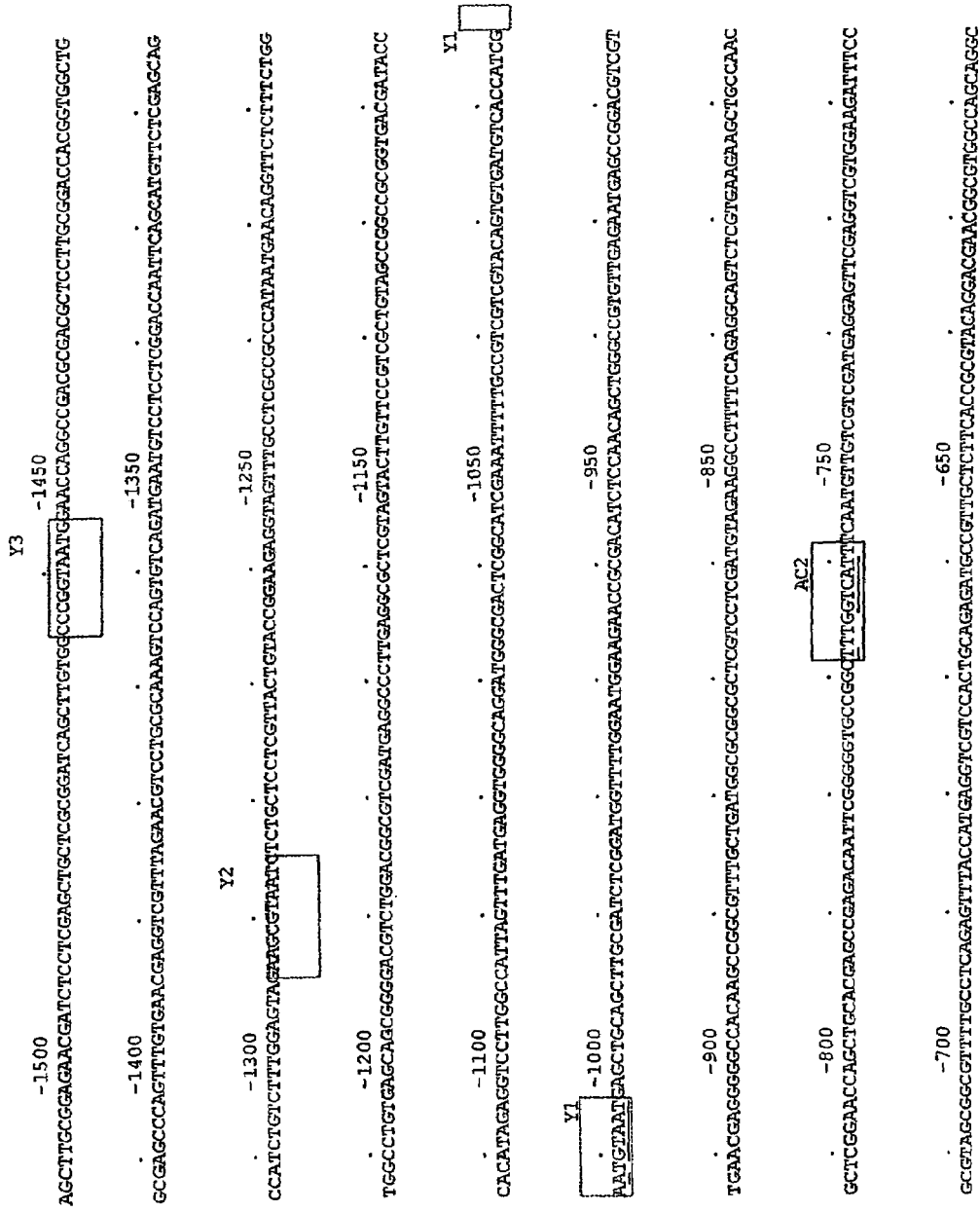

FIGS. 5a and 5b shows the sequence of the wild type MOX promoter with presumed TATA box and possible cryptic binding sites for bZip proteins used in the examples (SEQ ID NO: 25).

The site 1 framed with a continuous line (idAC1) and the site 1 framed with a short-dashed line (idY1) were modified.

AC: Cryptic ATF/CREB sequence.

idAC# The cryptic ATF/CREB sequence of each respective number was converted into an ideal ATF/CREB sequence.

Y: Cryptic YAP binding site.

idY# The cryptic YAP binding site of each respective number was converted into an ideal YAP binding site.

FIG. 6 shows the sequence of the wild type TPS1 promoter with presumed TATA box and possible cryptic binding sites for bZip proteins used in the examples (SEQ ID NO:26).

The site 1 framed with a continuous line (idAC1) and the site 1 framed with a short-dashed line (idC1) were modified.

AC: Cryptic ATF/CREB sequence.

idAC# The cryptic ATF/CREB sequence of each respective number was converted into an ideal ATF/CREB sequence.

C: Cryptic C/EBP binding site.

idC# The cryptic C/EBP binding site of each respective number was converted into an ideal C/EBP binding site.

Figure 7A:
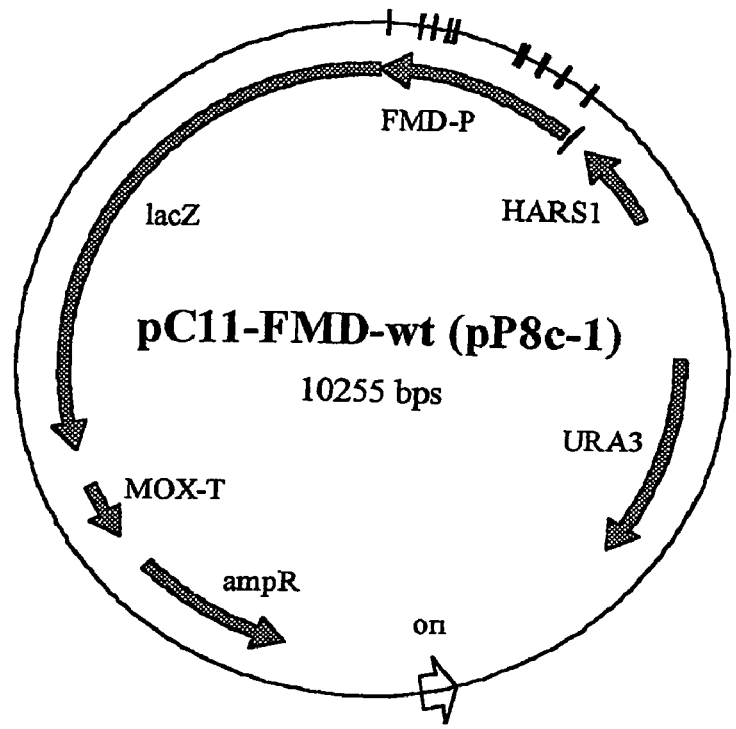
Figure 7B:
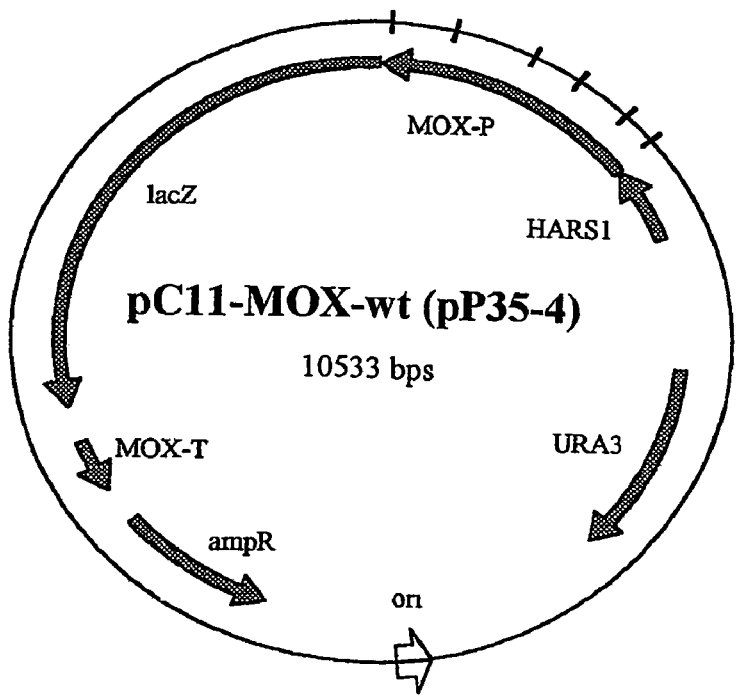
Figures 7C, 8:
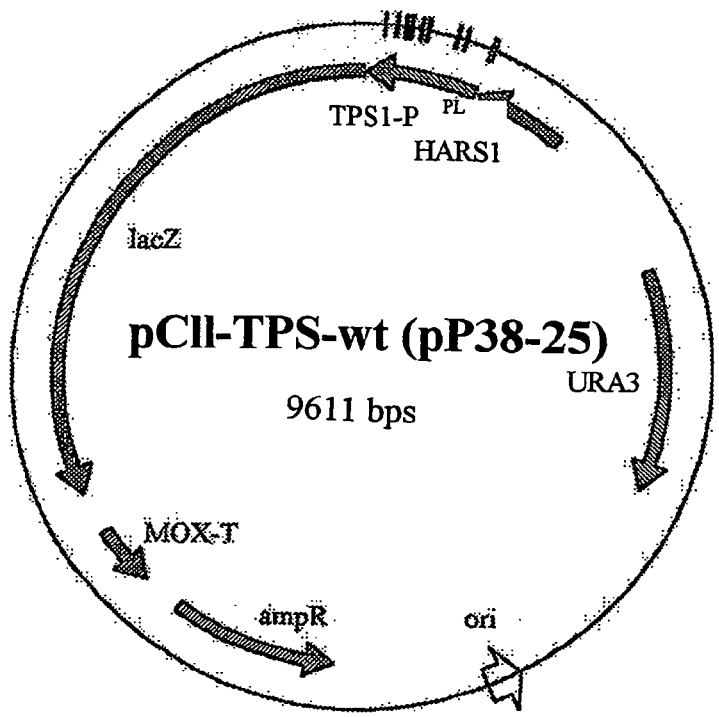

FIGS. 7A, 7B and 7C show gene maps of the lacZ reporter plasmids pCH-FMD, pC11-MOX and pCH-TPS1, which differ only in the respective promoter stated in the plasmid name.

FIG. 8 shows ideal binding sites for bZip proteins, the first column giving the designation, the middle column the idealised sequence and the right-hand column the biological origin of the sequence.

DETAILED DESCRIPTION OF THE INVENTION

The purpose of the present invention is therefore to provide a DNA comprising a promoter sequence which meets the individual requirements of methylotrophic yeast transcription systems.

According to the invention, this problem is solved by a DNA which comprises a promoter sequence which is derived from a wild type promoter of a methylotrophic yeast and whose transcription efficiency is modulated compared to the efficiency of the wild type promoter by introduction or modification of a DNA binding site.

It has been discovered that the transcription efficiency of the promoters of methylotrophic yeasts can be modulated. Such a modulation of the transcription efficiency can take place both by intensification and also by diminution of the activity of the promoter sequence and/or increased or decreased integration of the promoter sequence into the genome of a suitable host cell.

A wild type promoter from a methylotrophic yeast should be understood to mean a promoter which displays the same DNA sequence and the same transcription efficiency as the promoters from a naturally occurring methylotrophic yeast. Suitable wild type promoters are known to the skilled person from the specialist literature, through public deposition and through publication in databases. Thus for example the promoters FMD, MOX and TPS1 are disclosed in the European patent applications EP299108, EP173378 and EP1151112; the DHAS promoter is also described in EP173378. The promoters GAPDH and PMA1 are respectively in U.S. patent specification U.S. Pat. No. 935,789 and the document by Cox et al., Yeast 2000, September, 30; 16(13): 1191-203.

Examples of sequences of certain wild type FMD, MOX and TPS1 promoters can be taken from FIGS. 4 to 6. Since sequence analysis, in particular ten and more than twenty years ago sometimes contained errors, but possible errors are readily recognisable by checking with standardised routine methods, wild type promoters in the sense of the invention are understood to mean not only the wild type promoters disclosed by description in the state of the technology, but also the actually accessible wild type promoters.

Transcription efficiency should be understood to mean the production of transcript, i.e. mRNA per unit time. For the purpose of this application, it is determined as the quantity of a heterologous protein which is expressed in a suitable host cell per unit time under the control of a promoter, it being assumed that the translation efficiency depends only on the quantity of transcript available. The transcription efficiency is for example determined by standard procedures by quantitative determination of the heterologous protein or by evaluation of the signals of a reporter gene such as lacZ or phytase at different times.

Especially preferred is a DNA according to the invention, with which the transcription efficiency of the promoter sequence is increased compared to the efficiency of the wild type promoter by the insertion of a DNA binding site. In one embodiment, the DNA sequences according to the invention even display a considerably increased transcription efficiency compared to the wild type promoters. This is all the more surprising since the wild type promoters of methylotrophic yeasts already count among the most efficient promoters of all. A further increase, in particular so marked an increase, is therefore extremely surprising.

In a preferred embodiment, the invention concerns a DNA whose promoter sequence displays a transcription efficiency increased by at least the factor 1.5, preferably by at least the factor 2, and especially preferably by at least the factor 2.5, compared to the wild type promoter.

In another preferred embodiment, the invention concerns a DNA whose promoter sequence displays a decreased transcription efficiency compared to the wild type promoter, preferably a transcription efficiency decreased by at least the factor 0.5.

The promoter sequences are preferably a DNA according to the invention derived from a promoter from one of the genera *Candida, Hansenula, Pichia* or *Torulopsis*, especially preferably from a promoter from *Hansenula polymorpha* or *Candida boidinii*, and quite especially preferably from *Hansenula polymorpha*.

In a further preferred embodiment, the promoter sequence of a DNA according to the invention is derived from promoters of the group of the MOX, FMD, TPS1, DHAS, GAPDH and PMA1 promoters or similarly acting promoters from methylotrophic yeasts of the aforementioned genera.

Preferably a DNA according to the invention comprises at least one promoter sequence which is derived from a wild type promoter by the insertion, deletion and/or the exchange of at least one base, preferably by the exchange of one or two bases.

It has surprisingly been discovered that the wild type promoter sequences of methylotrophic yeasts have DNA regions which are similar but not identical to the DNA binding sites for transcription factors of the bZip protein class, these DNA regions naturally having no DNA binding function in the methylotrophic yeast. These so-called cryptic, i.e. similar but non-functional DNA binding sites for transcription factors of the bZip protein class, are a preferred option for the modification of the promoter transcription efficiency. It has been discovered that a modification of these cryptic DNA binding sites by deletion, insertion or exchange of individual or several base pairs can considerably modify the promoter transcription efficiency of methylotrophic yeasts. At the same time, in particular the formulation of this DNA binding site as a palindromic DNA shows a strong modification of the transcription activity.

In an especially preferred embodiment, the present invention therefore covers a DNA whose promoter sequence displays at least one DNA binding site, preferably a palindromic DNA binding site for transcription factors of the bZip protein class.

Transcription factors of the bZip protein class are for example described in Suckow et al., J. Mol. Biol. (1998) 276, 887-902. BZip proteins display a basic region which is responsible for the DNA recognition, and a C-terminal leucine "zip fastener" which is responsible for the specific dimer formation of these factors. Corresponding DNA binding sites for the bZip proteins are mostly palindromic or pseudopalindromic sequences with 10 or 9 base pairs.

Furthermore, it has been discovered that the transcription efficiency of promoter sequences of methylotrophic yeasts can be modulated by alteration of DNA regions whose motif is similar to the palindromic DNA binding sites of Zinkfinger proteins. These DNA regions can be modified by deletion, insertion or exchange of at least one base pair, as a result of which a palindromic DNA binding site for Zinkfinger proteins is preferably formed. In a further preferred embodiment, the promoter sequence of a DNA according to the invention therefore comprises at least one DNA binding site, preferably a palindromic DNA binding site, for Zinkfinger proteins.

Both the DNA motifs for transcription factors of the bZip protein class and also for Zinkfinger proteins are familiar to the skilled person in the field of molecular biology. Thus, in implementation of the present invention the skilled person can search the sequences of wild type promoters for DNA sequences which resemble the said motifs and by standard procedures modify these into functional and/or identical binding sites for bZip proteins or Zinkfinger proteins.

Especially preferred are DNA sequences according to the invention, whose promoter sequence displays at least one DNA binding site which essentially corresponds to the ATF/CREB binding site, the YAP binding site, the C/EBP binding site, the AP1 binding site or the G box. Examples of embodiments of these preferred binding sites are shown in FIG. 8 (example for AP1 or G box). Here "essentially" means that per strand not more than three, preferably two bases or only one base deviate(d) from the sequence at the said binding site.

In an especially preferred embodiment, the promoter sequence of a DNA according to the invention DNA comprises at least one palindromised DNA sequence, which is derived from the sequences given in SEQ ID No.: 1-SEQ ID No.: 23.

TABLE 1

| SEQ ID No: | Sequence | Reference designation |
|---|---|---|
| 1 | CACTGGTCAC | FMD AC1 |
| 2 | ATGACTTTGG | FMD AC2 |
| 3 | CTGACAGGGT | FMD AC3 |
| 4 | GTGACGGAAT | FMD AC4 |
| 5 | ATGACAGCAT | FMD AC5 |
| 6 | TGGAGGTCAA | FMD AC6 |
| 7 | ATGAGCCAGT | FMD AC7 |
| 8 | TCCAGATCAT | FMD AC8 |
| 9 | GGAGGCTCAG | FMD AC9 |
| 10 | ATTTCGTAAT | FMD Y1 |
| 11 | ATGGTGTCAT | MOX AC1 |
| 12 | CTTTGGTCAT | MOX AC2 |
| 13 | CGAATGTAAT | MOX Y1 |
| 14 | GAAGCGTAAT | MOX Y2 |
| 15 | GCCCGGTAAT | MOX Y3 |
| 16 | ATGGTGAGAT | TPSI AC1 |
| 17 | ATGAAAGGCT | TPSI AC2 |
| 18 | ATGAATCTCC | TPSI AC3 |
| 19 | ATGACGATAT | TPSI AC4 |
| 20 | ATTGACCAAT | TPSI C1 |
| 21 | ATTGCACCCA | TPSI C2 |
| 22 | GATTCGTAAT | TPSI Y1 |
| 23 | TTTTCGTCAT | TPSI AC5 |

Table 1 shows the preferred cryptic bZip sequences in the promoters FMD, MOX and TPS1 according to FIGS. 4 to 6.

Preferably, the palindromised sequence comprises at least 8 to 20, preferably 8 to 12, and especially preferably 10 bases.

The palindromised sequence can be symmetrical or unsymmetrical. Preferably it is symmetrical. The palindromised sequence preferably does not deviate from a completely palindromic sequence by more than 2 bases per strand, especially preferably by only one base and quite especially preferably not at all.

The DNA molecules according to the invention can for example by produced synthetically by common procedures, or else isolated from suitable DNA libraries and then mutated. The preparation of such libraries is likewise known to the skilled person. For example, an isolation is effected by preparing a probe with a length of at least 200-400 bp and the sequence of a wild type promoter of a methylotrophic yeast and a DNA library, in particular a genomic DNA library, is screened therewith. Such a probe can be prepared by means of a PCR (Polymerase Chain Reaction) with the use of suitable primers, which are each preferably at least 20-21 bp long and possess suitable sequences, and genomic or cDNA from methylotrophic yeasts as the "template".

Probes can for example be synthesised or produced by fragmentation of available wild type promoter DNA. It is also possible to screen directly with probes corresponding to parts of the promoter sequence. However, such a procedure is less preferable on account of defective conservation of the sequence within non-coding sections.

Furthermore, the DNA molecules according to the invention can comprise at least one DNA sequence for a homologous and/or heterologous gene lying under the transcription control of the promoter sequence.

A "heterologous gene" should be understood to mean the coding region of a structural gene which either does not lie under the control of the endogenous (homologous) promoter or is not expressed in the organism from which it is derived, or is expressed neither under the control of the endogenous promoter nor in the original organism.

Furthermore, the DNA molecule according to the invention can comprise a DNA sequence coding for a signal peptide, which ensures the export of the expressed protein, the DNA sequence coding for the signal peptide preferably being directly bound to the heterologous gene to be expressed. For the secretion and modification of many eukaryotic proteins, it is necessary to fuse the protein sequence at the N-terminus with a signal sequence, in order to direct the polypeptides into the secretion apparatus. For example, components from the *S. occidentalis* gene GAM1 or from a hormonal gene of the crab Carcinus maenas (CHH), which were successfully utilised for the secretion of hirudin (Weydemann et al., 1995) can be considered for this. Preferably, a DNA according to the invention comprises a secretion signal selected from the group GAM, GAM-kex2, CHH-kex2, MFα-prepro and the chicken lysozyme secretion signal. The aforementioned secretion signals are known to the skilled person from the state of the technology, for example from the European patent specifications EP 394,538 B1 and EP 716,705 B1 and the European patent application EP 725,822 A1. Further, the DNA according to the invention can comprise a terminator element, which contains signal structures for the RNA polymerase which lead to the termination of the transcription. Examples of usable terminator elements are the MOX or PHO1 terminator from *H. polymorpha*.

Also an object of the invention is a host cell which contains at least one DNA according to the invention, the host cell being a prokaryotic or a eukaryotic cell.

For example, the eukaryotic cell can be a plant cell. Preferably the cell is a fungal cell, especially preferably a yeast cell. Possible host cells for the implementation of the present invention are for example filamentous fungi such as for example *Aspergillus, Neurospora, Mucor, Trichoderma, Acremonium, Sordaria* and *Penicillium* or yeasts such as *Saccharomyces, Hansenula, Pichia, Torulopsis, Kluyveromyces, Schwanniomyces, Yarro-wia, Arxula, Trichosporon* and *Candida*.

Quite especially preferred is a methylotrophic yeast cell, especially one of the genus *Candida, Torulopsis, Hansenula* or *Pichia*. Most preferred is *Hansenula polymorpha*.

The present invention also concerns expression vectors, preferably plasmids, in which the vector comprises a DNA according to the invention.

In a preferred embodiment, such expression vectors include the phytase gene or LacZ as a reporter reading frame.

The present invention in addition provides a kit comprising:
(a) an expression vector according to the invention, which is suitable for the incorporation of a DNA which codes for a recombinant protein, and
(b) a host cell suitable for the production of the recombinant protein.

The incorporation of the DNA coding for a recombinant protein can be effected by all cloning methods known in the state of the technology. These are however not all described in detail, since they are part of the skilled person's normal stock in trade.

Further, a kit is provided, comprising
(a) an expression vector according to the invention, which is suitable for the incorporation of a DNA which codes for a recombinant protein, and
(b) a host cell which is suitable for the production of the recombinant protein under the transcription control of the promoter sequence.

The DNA molecules, host cells, expression vectors and kits according to the invention can be used for the recombinant expression of a gene under the control of the promoter sequence for the production of one or several proteins.

The present invention thus also concerns the use of the objects according to the invention for the production of proteins.

"Recombinant expression in a suitable host cell" should be understood to mean all expression methods in known expression systems known in the state of the technology, which could be used here. These are however not all described in detail, since they are part of the skilled person's normal stock in trade.

Also an object of the invention is a process for the production of one or several proteins, comprising:
(i) the cloning of at least one DNA which codes for a recombinant protein, into an expression vector according to the invention, so that the cloned DNA lies under the transcription control of the promoter sequence;
(ii) the introduction of the expression vector obtained in (i) into a host cell which is suitable for the production of the recombinant protein, optionally after induction of the promoter sequence;
(iii) the cultivation of the host cell obtained in (ii);
(iv) and optionally the induction of the promoter sequence in a manner in itself known.

In a preferred embodiment, the process according to the invention includes the following steps:
(i) the introduction of an expression vector according to the invention into a host cell which is suitable for the production of the recombinant protein, optionally after induction of the promoter sequence;
(ii) the cultivation of the host cell obtained in (i);
(iii) and optionally the induction of the promoter sequence in a manner in itself known.

A further aspect of the present invention concerns processes for the production of the expression vectors according to the invention, comprising (a) the insertion of a DNA according to the invention into an expression vector; or (b) the modification of a promoter sequence of a methylotrophic yeast in an expression vector by insertion, preferably deletion and/or exchange of at least one base pair in a manner it itself known, so that a palindromic binding site is produced, preferably a palindromic binding site for transcription factors of the bZip proteins or for Zinkfinger proteins; and (c) optionally the introduction of a heterologous gene in a manner in itself known into an expression vector, so that the heterologous gene lies under the transcription control of the DNA from (a) or of the modified promoter sequence from (b).

EXPERIMENTAL EXAMPLES

Introduction

The following examples show the change in the transcription efficiency of promoters of methylotrophic yeasts such as the FMD, MOX und TPS1 promoters due to conversion of individual or several cryptic DNA binding sites into their palindromic and thus formally idealised derivatives.

Preparation of Modified Wild Type Promoters

The wild type promoters to be modified (see FIGS. 4 (FMD), 5 (MOX), and 6 (TPS1)) were transferred into pUC18 and there deliberately modified in a manner in itself known by means of PCR mutagenesis. After verification of the exchanges by sequence analysis, the modified promoters were subcloned into expression plasmids which contained either phytase or lacZ as reporter reading frames. The two series of reporter plasmids created in this way differ only in their promoter sequences (see for example for lacZ as reporter gene the FIG. 7A (FMD promoter), FIG. 7B (MOX promoter) and FIG. 7C (TPS1 promoter)).

Integrative Test System

In order to be able to compare promoters with one another objectively, the reporter gene doses of the strains to be compared must be comparable. The following integrative test system was therefore constructed, which is suitable both for lacZ and also for phytase reporter plasmids. *H. polymorpha* was transformed with each reporter plasmid and 48 strains with genomically integrated plasmid DNA were created per construct. These sets of 48 strains were then subjected to a reporter protein test. This test yielded two pieces of information: firstly the construct-determined reporter gene expression strengths under the tested condition as an endpoint determination, and secondly the identification of the two strains in each set with the highest reporter gene expression rates. These strains were then subjected to further comparative experiments. Furthermore, the copy number of the integrated reporter plasmid in them was determined, in order to exclude the possibility that of any intensified promoter activities being attributable to a gene dosage effect.

Determination of FMD Promoter Variants with Increased Activity and/or Modified Regulation The strains with id1 or id1-4 in the strain designation contained expression cassettes with FMD promoter variants with deliberate modifications in the region of cryptic bZip binding sites (here: in the region of the ATF/CREB sequences 1 to 4). The various promoters were tested both in combination with lacZ and also in combination with the phytase gene.

For the quantification of the β-galactosidase, ONPG measurements (ONPG: ortho-nitrophenyl-β-D-galactopyranoside; J. H. Miller (1972) Experiments in Molecular Genetics. Cold Spring Harbour Laboratory Press. Cold Spring Harbour, N.Y., USA) were carried out with intracellular soluble fractions.

For phytase, the phytase test was carried out with culture supernatants (A. F. Mayer, K. Hellmuth, H. Schlieker, R. Lopez-Ulibarry, S. Oertel, U. Dahlems, A. W. M. Strasser and A. P. G. M. van Loon (1999) An expression System matures: a highly efficient and cost-effective process for phytase production by recombinant strains of *Hansenula polymorpha*. Biotechnology and Bioengineering 63, 373-381; L. Pasamontes, M. Haiker, M. Wyss, M. Tessier and A. P. G. M. van Loon (1997) Gene cloning, purification and characterization of a heat-stable phytase from the fungus *Aspergillus fumigatus*. Appl. Environ. Microbiol. 63, 1696-1700).

Independently of the reporter gene, two different promoter characteristics were analysed: strength and regulation. The determination of the relative copy numbers of the integrated plasmids showed that the compared strains with modified promoters contained fewer or the same number of copies as the respective primary strain with the wild type promoter.

Strength of the Modified FMD Promoters

Figure 1A:
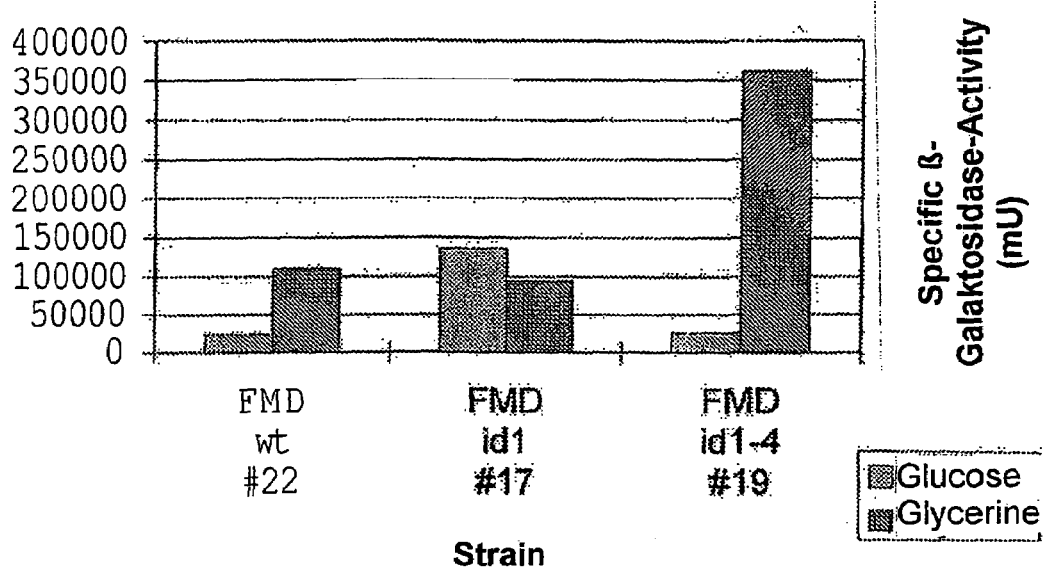
FIGS. 1A and 1B show the expression efficiency for strains with the reporter genes lacZ (FIG. 1A) and phytase (FIG. 1B) under the control of the FMD promoter variants (FMD id1 and FMD id1-4) according to the invention compared graphically with the wild type promoter (FMD wt, strain with wild type promoter) after 24 hours' growth on glucose (light grey) or glycerine (dark grey)).
Figure 1B:
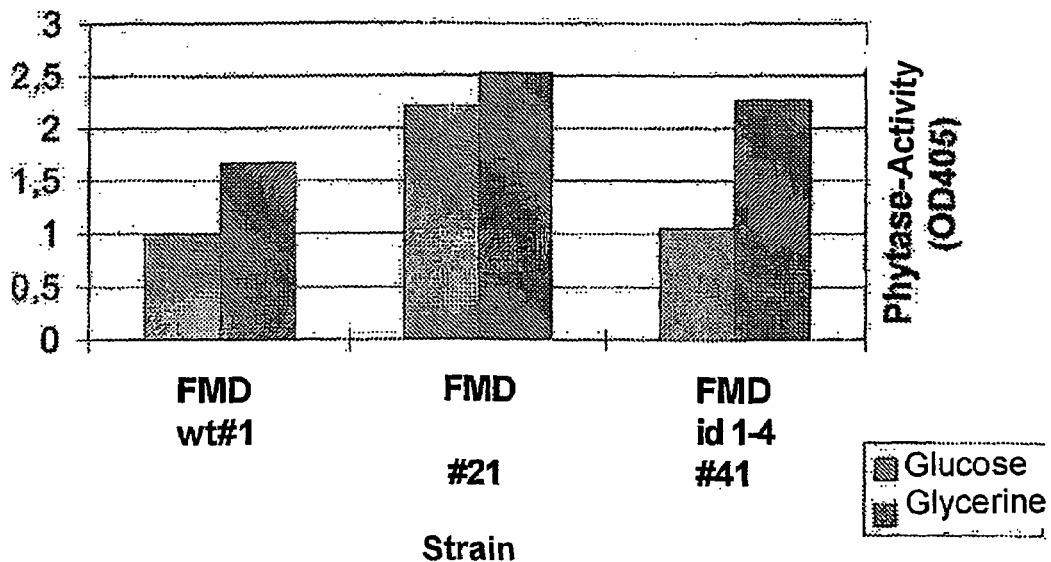

For the assessment of each FMD promoter modified according to the invention compared to the strength of the wild type FMD promoter, the following experiment was performed. The strongest strain for each reporter plasmid was cultivated for 48 hours on glucose or on glycerine as the carbon source. After 4, 24 and 48 hours, cells (lacZ) or culture supernatant (phytase gene) were harvested. For lacZ, starting from the harvested cells, intracellular soluble fractions were prepared, with which an ONPG measurement was then performed for the determination of the specific β-galactosidase activity. For phytase, a phosphatase test, in which the harvested culture supernatants were used directly, was performed. FIGS. 1A and B show the absolute measured values for the strains tested after 24 hours' growth on glucose (FIG. 1A) and glycerine (FIG. 1B). Both with lacZ and also with phytase gene, peak values which lie markedly above the values attained with the wild type FMD promoter are attained with the modified promoters. This effect was in general more pronounced with lacZ (FIG. 1B) than with phytase gene (FIG. 1A). This occurs because phytase is a secretory glycoprotein, for which a large number of transport and modification steps must be completed between the transcription of the gene and the appearance of the active gene product in the culture supernatant, which are not necessary for the generation of the cytosol-located β-galactosidase. Both with phytase gene and also with lacZ, individual FMD promoter variants reach higher activities on glucose than the wild type promoter on glycerine. In the case of lacZ, the peak values attained with the wild type promoter were exceeded by a factor of up to 3.5, and in the case of phytase gene by a factor of up to 2.5 (see FIGS. 1A and 1B).

Regulation of Modified FMD Promoters

The FMD promoter variants tested showed regulation deviating to some extent from that of the wild type promoter. As a measure for the regulation, the quotient of the values measured after 24 hours' cultivation on glycerine and glucose was generated. A factor of 1 signifies constitutivity, based on the carbon sources studied. Higher factors indicate that the given promoter displays higher activity on glycerine than on glucose. The order of the regulation factors measured with the various FMD promoter variants is qualitatively identical with both reporter genes (lacZ and phytase gene) (FIG. 2): id1-4>wt>id1.

The promoter id1 is approximately constitutive, while the promoter id1-4 displays a higher regulation than the wild type FMD promoter with both reporter genes (see FIG. 2).

Thus it has been shown that according to the invention both the strength and also the regulation of methylotrophic promoters, in this case the FMD promoter, can be significantly modified.

MOX and TPS1 Promoter Variants with Increased Activity on Media with Glucose as Carbon Source To demonstrate the transferability of the modulability of efficiency demonstrated above for FMD promoters to other promoters of methylotrophic yeasts, the transcription efficiency of a MOX promoter and a TPS1 promoter was also modulated according to the invention. In the sequence of the MOX promoter of *H. polymorpha*, five cryptic binding sites for bZip proteins were identified, namely two motifs with similarity to the ATF/CREB sequence and three motifs with similarity to the YAP binding site (see FIG. 5). By analogy to the modifications carried out on the FMD promoter, two of these sequence motifs were palindromised. The resulting promoter variants MOX-idA/CI and MOX-idY1 and the wild type MOX promoter were transferred into the lacZ reporter plasmid, as already described for the FMD promoter, in such a manner that they took over control of the reporter gene.

In the sequence of the TPS1 promoter, a total of eight possible cryptic bZip motifs were identified (see FIG. 6). Five of the motifs described in this example have similarity to the ATF/CREB sequence, two to the C/EBP binding site and one to the YAP binding site. For this promoter, two variants were constructed, each with a palindromised sequence motif, TPS-idA/CI and TPS-idCI.

Further cryptic bZip or Zinkfinger motifs are accessible to the skilled person through more detailed analysis, e.g. by recourse to computer-supported comparison algorithms.

48 strains were generated per construct. As described for the FMD constructs, the strains with the highest reporter gene activities were firstly determined by means of an X-Gal overlay test, and these were then analysed in more detail. FIG. 3 shows an X-Gal overlay test of five of these strains from each set, which had previously been grown at 37° C. on YNB/glucose plates. Both with the MOX and also with the TSP1 promoter, it was found that the palindromisation of the first (nearest to the TATA box) ATF/CREB sequence-like motif under the tested condition resulted in a visible increase in the promoter activity, compared to the respective wild type promoter (see FIG. 3). With other carbon sources tested, this effect could not be observed. This result shows that the transcription properties of MOX and TPS1 promoters can also be modified by modification, in particular palindromisation, of already present cryptic DNA binding sites.

The disclosures of each and every patent, patent application, and publication cited herein are hereby incorporated herein by reference in their entirety.

What is claimed is:

1. A DNA comprising at least one promoter sequence which is derived from a wild type promoter of *Hansenula polymorpha*, selected from the group consisting of the MOX, FMD, and TPS1 promoters, characterised in that the transcription efficiency of this promoter sequence compared to the efficiency of the wild type promoter is increased by modification of a DNA binding site for transcription factors, wherein the increase is achieved by palindromisation of at least one of the DNA sequences stated in SEQ ID NO: 1-SEQ ID NO: 23, and wherein the palindromised sequence does not deviate from a completely palindromic sequence by more than 2 bases per strand.

2. The DNA according to claim 1, characterised in that the transcription efficiency of the promoter sequence compared to the efficiency of the wild type promoter is increased by at least the factor 1.5.

3. The DNA according to claim 1, characterised in that the palindromised sequence is symmetrical and deviates from a completely palindromic sequence in not more than one base per strand.

4. The DNA according to claim 1, characterised in that it further comprises at least one DNA sequence for a homologous and/or heterologous gene lying under the transcription control of the promoter sequence.

5. The DNA according to claim 1, characterised in that it further comprises a DNA sequence coding for a secretion signal.

6. The DNA according to claim 5, characterised in that the secretion signal is selected from the group GAM, GAM-kex2, CHH-kex2, MFα-prepro and the chicken lysozyme secretion signal.

7. A host cell, characterised in that the host cell contains at least one DNA comprising at least one promoter sequence which is derived from a wild type promoter of *Hansenula polymorpha*, selected from the group consisting of the MOX, FMD, and TPS1 promoters, characterised in that the transcription efficiency of this promoter sequence compared to the efficiency of the wild type promoter is increased by modification of a DNA binding site for transcription factors, wherein the increase is achieved by palindromisation of at least one of the DNA sequences stated in SEQ ID NO: 1-SEQ ID NO: 23, and wherein the palindromised sequence does not deviate from a completely palindromic sequence by more than 2 bases per strand.

8. The host cell according to claim 7, characterised in that said DNA is integrated into the genome of the host cell, or is present in the host cell as an extrachromosomal DNA molecule.

9. The host cell according to claim 7, characterised in that the host cell is a yeast cell of the genera *Candida, Torulopsis, Hansenula* or *Pichia*.

10. An expression vector characterised in that said vector comprises a DNA comprising at least one promoter sequence which is derived from a wild type promoter of *Hansenula polymorpha*, selected from the group consisting of the MOX, FMD, and TPS1 promoters, characterised in that the transcription efficiency of this promoter sequence compared to the efficiency of the wild type promoter is increased by modification of a DNA binding site for transcription factors, wherein the increase is achieved by palindromisation of at least one of the DNA sequences stated in SEQ ID NO: 1-SEQ ID NO: 23, and wherein the palindromised sequence does not deviate from a completely palindromic sequence by more than 2 bases per strand.

11. The expression vector according to claim 10, characterised in that the vector contains a phytase gene or lacZ as a reporter reading frame.

12. A kit, comprising:
(a) an expression vector, which is suitable for the cloning of a DNA which codes for a recombinant protein, wherein the expression vector comprises a DNA comprising at least one promoter sequence which is derived from a wild type promoter of *Hansenula polymorpha*, selected from the group consisting of the MOX, FMD, and TPS1 promoters, characterised in that the transcription efficiency of this promoter sequence compared to the efficiency of the wild type promoter is increased by modification of a DNA binding site for transcription factors, wherein the increase is achieved by palindromisation of at least one of the DNA sequences stated in SEQ ID NO: 1-SEQ ID NO: 23, and wherein the palindromised sequence does not deviate from a completely palindromic sequence by more than 2 bases per strand; and
(b) a host cell suitable for the production of the recombinant protein.

13. A method for the production of at least one protein, comprising:
(i) introduction of an expression vector comprising a DNA into a host cell which is suitable for the production of the recombinant protein, optionally after induction of the promoter sequence, wherein the DNA comprises at least one promoter sequence which is derived from a wild type promoter of *Hansenula polymorpha*, selected from the group consisting of the MOX, FMD, and TPS1 promoters, characterised in that the transcription efficiency of this promoter sequence compared to the efficiency of the wild type promoter is increased by modification of a DNA binding site for transcription factors, wherein the increase is achieved by palindromisation of at least one of the DNA sequences stated in SEQ ID NO: 1-SEQ ID NO: 23, and wherein the palindromised sequence does not deviate from a completely palindromic sequence by more than 2 bases per strand;
(ii) cultivation of the host cell obtained in (i); and
(iii) optionally induction of the promoter, as a result of which the protein or proteins is/are produced by the host cell.

14. A method for the production of at least one protein, comprising:
(i) construction of an expression vector containing a DNA, wherein the DNA comprises at least one promoter sequence which is derived from a wild type promoter of *Hansenula polymorpha*, selected from the group consisting of the MOX, FMD, and TPS1 promoters, characterised in that the transcription efficiency of this promoter sequence compared to the efficiency of the wild type promoter is increased by modification of a DNA binding site for transcription factors, wherein the increase is achieved by palindromisation of at least one of the DNA sequences stated in SEQ ID NO: 1-SEQ ID NO: 23, wherein the palindromised sequence does not deviate from a completely palindromic sequence by more than 2 bases per strand, and wherein the DNA further comprises at least one DNA sequence for a homologous and/or heterologous gene lying under the transcription control of the promoter sequence;
(ii) introduction of said expression vector into a host cell which is suitable for the production of a recombinant protein, optionally after induction of the promoter sequence;
(iii) cultivation of the host cell obtained in (ii); and (iv) optionally induction of the promoter sequence, as a result of which the protein or proteins is/are produced by the host cell.

15. A method for the production of expression vectors, comprising:
   (i) the modification of a promoter sequence of *Hansenula polymorpha* selected from the group consisting of the MOX, FMD, and TPS1 promoters, in an expression vector by insertion, deletion and/or exchange of at least one base, wherein the transcription efficiency of the promoter sequence compared to the efficiency of the wild type promoter is increased by modification of a DNA binding site for transcription factors, wherein the increase is achieved by palindromisation of at least one of the DNA sequences stated in SEQ ID NO: 1-SEQ ID NO: 23, and wherein the palindromised sequence does not deviate from a completely palindromic sequence by more than 2 bases per strand; and
   (ii) optionally the introduction of a heterologous gene into said expression vector, so that the heterologous gene lies under the transcription control of the DNA from (i);

wherein the expression vector comprises a DNA comprising at least one promoter sequence which is derived from a wild type promoter of *Hansenula polymorpha*, selected from the group consisting of the MOX, FMD, and TPS1 promoters, characterised in that the transcription efficiency of this promoter sequence compared to the efficiency of the wild type promoter is increased by modification of a DNA binding site for transcription factors, wherein the increase is achieved by palindromisation of at least one of the DNA sequences stated in SEQ ID NO: 1-SEQ ID NO: 23, and wherein the palindromised sequence does not deviate from a completely palindromic sequence by more than 2 bases per strand.

16. The kit of claim 12, wherein the expression vector contains a phytase gene or lacZ as a reporter reading frame.

17. The method of claim 15, wherein the expression vector contains a phytase gene or lacZ as a reporter reading frame.

* * * * *

SEQUENCE LISTING

<160> NUMBER OF SEQ ID NOS: 30

<210> SEQ ID NO 1
<211> LENGTH: 10
<212> TYPE: DNA
<213> ORGANISM: Hansenula polymorpha
<220> FEATURE:
<223> OTHER INFORMATION: Description of the sequence: FMD-Promoter
      segment

<400> SEQUENCE: 1
cactggtcac                                                        10

<210> SEQ ID NO 2
<211> LENGTH: 10
<212> TYPE: DNA
<213> ORGANISM: Hansenula polymorpha
<220> FEATURE:
<223> OTHER INFORMATION: Description of the sequence: FMD-Promoter
      segment

<400> SEQUENCE: 2
atgactttgg                                                        10

<210> SEQ ID NO 3
<211> LENGTH: 10
<212> TYPE: DNA
<213> ORGANISM: Hansenula polymorpha
<220> FEATURE:
<223> OTHER INFORMATION: Description of the sequence: FMD-Promoter
      segment

<400> SEQUENCE: 3
ctgacaggt                                                         10

<210> SEQ ID NO 4
<211> LENGTH: 10
<212> TYPE: DNA
<213> ORGANISM: Hansenula polymorpha
<220> FEATURE:
<223> OTHER INFORMATION: Description of the sequence: FMD-Promoter
      segment

<400> SEQUENCE: 4
gtgacggaat                                                          10

<210> SEQ ID NO 5
<211> LENGTH: 10
<212> TYPE: DNA
<213> ORGANISM: Hansenula polymorpha
<220> FEATURE:
<223> OTHER INFORMATION: Description of the sequence: FMD-Promoter
      segment

<400> SEQUENCE: 5
atgacagcat                                                          10

<210> SEQ ID NO 6
<211> LENGTH: 10
<212> TYPE: DNA
<213> ORGANISM: Hansenula polymorpha
<220> FEATURE:
<223> OTHER INFORMATION: Description of the sequence: FMD-Promoter
      segment

<400> SEQUENCE: 6
tggaggtcaa                                                          10

<210> SEQ ID NO 7
<211> LENGTH: 10
<212> TYPE: DNA
<213> ORGANISM: Hansenula polymorpha
<220> FEATURE:
<223> OTHER INFORMATION: Description of the sequence: FMD-Promoter
      segment

<400> SEQUENCE: 7
atgagccagt                                                          10

<210> SEQ ID NO 8
<211> LENGTH: 10
<212> TYPE: DNA
<213> ORGANISM: Hansenula polymorpha
<220> FEATURE:
<223> OTHER INFORMATION: Description of the sequence: FMD-Promoter
      segment

<400> SEQUENCE: 8
tccagatcat                                                          10

<210> SEQ ID NO 9
<211> LENGTH: 10
<212> TYPE: DNA
<213> ORGANISM: Hansenula polymorpha
<220> FEATURE:
<223> OTHER INFORMATION: Description of the sequence: FMD-Promoter
      segment

<400> SEQUENCE: 9
ggaggctcag                                                          10

```
<210> SEQ ID NO 10
<211> LENGTH: 10
<212> TYPE: DNA
<213> ORGANISM: Hansenula polymorpha
<220> FEATURE:
<223> OTHER INFORMATION: Description of the sequence: FMD-Promoter
      segment

<400> SEQUENCE: 10
atttcgtaat                                                              10

<210> SEQ ID NO 11
<211> LENGTH: 10
<212> TYPE: DNA
<213> ORGANISM: Hansenula polymorpha
<220> FEATURE:
<223> OTHER INFORMATION: Description of the sequence: MOX-Promoter
      segment

<400> SEQUENCE: 11
atggtgtcat                                                              10

<210> SEQ ID NO 12
<211> LENGTH: 10
<212> TYPE: DNA
<213> ORGANISM: Hansenula polymorpha
<220> FEATURE:
<223> OTHER INFORMATION: Description of the sequence: MOX-Promoter
      segment

<400> SEQUENCE: 12
ctttggtcat                                                              10

<210> SEQ ID NO 13
<211> LENGTH: 10
<212> TYPE: DNA
<213> ORGANISM: Hansenula polymorpha
<220> FEATURE:
<223> OTHER INFORMATION: Description of the sequence: MOX-Promoter
      segment

<400> SEQUENCE: 13
cgaatgtaat                                                              10

<210> SEQ ID NO 14
<211> LENGTH: 10
<212> TYPE: DNA
<213> ORGANISM: Hansenula polymorpha
<220> FEATURE:
<223> OTHER INFORMATION: Description of the sequence: MOX-Promoter
      segment

<400> SEQUENCE: 14
gaagcgtaat                                                              10

<210> SEQ ID NO 15
<211> LENGTH: 10
<212> TYPE: DNA
<213> ORGANISM: Hansenula polymorpha
<220> FEATURE:
<223> OTHER INFORMATION: Description of the sequence: MOX-Promoter
      segment

<400> SEQUENCE: 15
gcccggtaat                                                              10
```

```
<210> SEQ ID NO 16
<211> LENGTH: 10
<212> TYPE: DNA
<213> ORGANISM: Hansenula polymorpha
<220> FEATURE:
<223> OTHER INFORMATION: Description of the sequence: TPS1-Promoter
      segment

<400> SEQUENCE: 16
atggtgagat                                                          10

<210> SEQ ID NO 17
<211> LENGTH: 10
<212> TYPE: DNA
<213> ORGANISM: Hansenula polymorpha
<220> FEATURE:
<223> OTHER INFORMATION: Description of the sequence: TPS1-Promoter
      segment

<400> SEQUENCE: 17
atgaaaggct                                                          10

<210> SEQ ID NO 18
<211> LENGTH: 10
<212> TYPE: DNA
<213> ORGANISM: Hansenula polymorpha
<220> FEATURE:
<223> OTHER INFORMATION: Description of the sequence: TPS1-Promoter
      segment

<400> SEQUENCE: 18
atgaatctcc                                                          10

<210> SEQ ID NO 19
<211> LENGTH: 10
<212> TYPE: DNA
<213> ORGANISM: Hansenula polymorpha
<220> FEATURE:
<223> OTHER INFORMATION: Description of the sequence: TPS1-Promoter
      segment

<400> SEQUENCE: 19
atgacgatat                                                          10

<210> SEQ ID NO 20
<211> LENGTH: 10
<212> TYPE: DNA
<213> ORGANISM: Hansenula polymorpha
<220> FEATURE:
<223> OTHER INFORMATION: Description of the sequence: TPS1-Promoter
      segment

<400> SEQUENCE: 20
attgaccaat                                                          10

<210> SEQ ID NO 21
<211> LENGTH: 10
<212> TYPE: DNA
<213> ORGANISM: Hansenula polymorpha
<220> FEATURE:
<223> OTHER INFORMATION: Description of the sequence: TPS1-Promoter
      segment

<400> SEQUENCE: 21
attgcaccca                                                          10

<210> SEQ ID NO 22
```

-continued

```
<211> LENGTH: 10
<212> TYPE: DNA
<213> ORGANISM: Hansenula polymorpha
<220> FEATURE:
<223> OTHER INFORMATION: Description of the sequence: TPS1-Promoter
      segment

<400> SEQUENCE: 22
gattcgtaat                                                              10

<210> SEQ ID NO 23
<211> LENGTH: 10
<212> TYPE: DNA
<213> ORGANISM: Hansenula polymorpha
<220> FEATURE:
<223> OTHER INFORMATION: Description of the sequence: TPS1-Promoter
      segment

<400> SEQUENCE: 23
ttttcgtcat                                                              10

<210> SEQ ID NO 24
<211> LENGTH: 1230
<212> TYPE: DNA
<213> ORGANISM: Hansenula polymorpha
<220> FEATURE:
<223> OTHER INFORMATION: Description of the sequence: FMD-Promoter

<400> SEQUENCE: 24
agcttgagca agttctcaaa cgcgggtttg tcgacgctct cccttatgcg actcctgcat        60
taggaagcag cccagtagta ggttgaggcc gttgagcacc gccgccgcaa ggaatggtgt       120
cgacgcggag aacgatctcc tgacgcggga aacgatctc ctcgagatcc aggaagcgca       180
acgacgcggg gaatttcgta atcttccccg aggaaaaccg cttcccaaag atttcaccgg       240
caataacgcc ttcattgacc gcacagagta ccacttgaac aacattctga acggcagga        300 ggcggttccg ccgtggatag agaaacaggg cagtgtggag gctcagatcc gccagtttcg       360
gcgccagctc gactccgatt ggacactgca ggccgtgcac atcgtttgcg agaaacactc       420
gaagaaaagc gacacggaca agatccagat catgagccag tacgccgagg cagagcgcaa       480
caataactcg agttatacga agctgcgcag cagccaatgg gaacagaaat acagcaacta       540
tctggaggtc aaattaaaag cgctgaatga cagcatccga ggttataatc tgcaggctcc       600
tttggcatcg cagaaactgt atctaaacgc aaactccgag ctggaaaaat gttaccggcg       660
atgcgcggac aatttagagg cggcgatcaa gaaacacctg ctgggcgagc agtctggagc       720
acagtcttcg atgggcccga gatcccaccg cgttcctggg taccgggacg tgaggcagcg       780
cgacatccat caaatatacc aggcgccaac cgagtctctc ggaaaacagc ttctggatat       840
cttccgctgg cggcgcaacg acgaataata gtccctggag gtgacggaat atatatgtgt       900
ggagggtaaa tctgacaggg tgtagcaaag gtaatatttt cctaaaacat gcaatcggct       960
gccccgcaac gggaaaaaga atgactttgg cactcttcac cagagtgggg tgtcccgctc      1020
gtgtgtgcaa ataggctccc actggtcacc ccggattttg cagaaaaaca gcaagttccg      1080
gggtgtctca ctggtgtccg ccaataagag gagccggcag gcacggagtc tacatcaagc      1140
tgtctccgat acactcgact accatccggg tctctcagag aggggaatgg cactataaat      1200
accgcctcct gcgctctctg cttcatcggg                                       1230

<210> SEQ ID NO 25
<211> LENGTH: 1508
```

```
<212> TYPE: DNA
<213> ORGANISM: Hansenula polymorpha
<220> FEATURE:
<221> NAME/KEY: misc_feature
<222> LOCATION: (1)..(1508)
<223> OTHER INFORMATION: n = a or g or c or t/u, unknown or else
<220> FEATURE:
<223> OTHER INFORMATION: Description of the sequence: MOX-Promoter

<400> SEQUENCE: 25
agcttgcgga gaacgatctc ctcgagctgc tcgcggatca gcttgtggcc cggtaatgga      60
accaggccga cgcgacgctc cttgcggacc acggtggctg gcgagcccag tttgtgaacg     120
aggtcgttta gaacgtcctg cgcaaagtcc agtgtcagat gaatgtcctc ctcggaccaa     180
ttcagcatgt tctcgagcag ccatctgtct ttggagtaga agcgtaatct ctgctcctcg     240
ttactgtacc ggaagaggta gtttgcctcg ccgcccataa tgaacaggtt ctctttctgg     300
tggcctgtga gcagcgggga cgtctggacg gcgtcgatga ggcccttgag gcgctcgtag     360
tacttgttcc gtcgctgtag ccggccgcgg tgacgatacc cacatagagg tccttggcca     420
ttagtttgat gaggtggggc aggatgggcg actcggcatc gaaattttg ccgtcgtcgt      480
acagtgtgat gtcaccatcg aatgtaatga gctgcagctt gcgatctcgg atggttttgg     540
aatggaagaa ccgcgacatc tccaacagct gggccgtgtt gagaatgagc cggacgtcgt     600
tgaacgaggg ggccacaagc cggcgtttgc tgatggcgcg gcgctcgtcc tcgatgtaga     660
aggcctttc cagaggcagt ctcgtgaaga agctgccaac gctcggaacc agctgcacga      720
gccgagacaa ttcggggtg ccggctttgg tcatttcaat gttgtcgtcg atgaggagtt      780
cgaggtcgtg gaagatttcc gcgtagcggc gttttgcctc agagtttacc atgaggtcgt     840
ccactgcaga gatgccgttg ctcttcaccg cgtacaggac gaacggcgtg gccagcaggc     900
ccttgatcca ttctatgagg ccatctcgac ggtgttcctt gagtgcgtac tccactctgt     960
agcgactgga catctcgaga ctgggcttgc tgtgctggat gcaccaatta attgttgccg    1020
catgcatcct tgcaccgcaa gttttaaaa cccactcgct ttagccgtcg cgtaaaactt     1080
gtgaatntgg caactgaggg ggttctgcag ccgcaaccga acttttcgct tcgaggacgc    1140
agctggatgg tgtcatgtga ggctctgttt gctggggtag cctacaacgt gaccttgcct    1200
aaccggacgg cgctacccac tgctgtctgt gcctgctacc agaaaatcac cagagcagca    1260
gagggccgat gtggcaactg gtggggtgtc ggacaggctg tttctccaca gtgcaaatgc    1320
gggtgaaccg gccagaaagt aaattcttat gctaccgtgc agcgactccg acatcccag     1380
ttttgccct acttgatcac agatggggtc agcgctgccg ctaagtgtac ccaaccgtcc     1440
ccacacggtc catctataaa tactgctgcc agtgcacggt ggtgacatca atctaaagta    1500
caaaaacg                                                             1508

<210> SEQ ID NO 26
<211> LENGTH: 566
<212> TYPE: DNA
<213> ORGANISM: Hansenula polymorpha
<220> FEATURE:
<223> OTHER INFORMATION: Description of the sequence: TPS1-Promoter

<400> SEQUENCE: 26
gatgtcaaaa tggggatca caaaagtaca ctcacgagga aaatcaaaac cttctcgtac       60
```

```
ctttaacaca tacggaaatg atcgatcgat ttgagaagat tcctcaatga ttttcgtcat    120
atataggtat ctgaggtatt tatggaccga ttcgtaataa catcatatac atcgcgcttt    180
gtccctgtcc cagagatttc gatgaaaaaa gcgaattta ttctaatatt tgaagcatgc     240
```
<br>


```
ctttaacaca tacggaaatg atcgatcgat ttgagaagat tcctcaatga ttttcgtcat    120
atataggtat ctgaggtatt tatggaccga ttcgtaataa catcatatac atcgcgcttt    180
gtccctgtcc cagagatttc gatgaaaaaa gcgaatttta ttctaatatt tgaagcatgc    240
caaacatggg gcagttgatt tgtgtgaggg taaaatatca tgaattgcac ccatcaaatg    300
cagcaagata ttgaccaatc ctataataga aaacagactt accacaaata gattgtgatg    360
acgatattat gaatctccag atgaaaggct cgaaagctat gaagcctctt gaaacttttc    420
atggtgagat aatattttcg aaatttccac gaacttctaa aacgcaatta ttgaatataa    480
aggaaaaata atatttccat atagcaagca aatcaagctg cactcctcat ccttaaaact    540
aataaatctt acccatttga taccag                                          566

<210> SEQ ID NO 27
<211> LENGTH: 10
<212> TYPE: DNA
<213> ORGANISM: Hansenula polymorpha
<220> FEATURE:
<223> OTHER INFORMATION: Description of the sequence: idealised
      MOX-Promoter segment

<400> SEQUENCE: 27
atgacgtcat                                                            10

<210> SEQ ID NO 28
<211> LENGTH: 10
<212> TYPE: DNA
<213> ORGANISM: Hansenula polymorpha
<220> FEATURE:
<223> OTHER INFORMATION: Description of the sequence: idealised
      MOX-Promoter segment

<400> SEQUENCE: 28
attacgtaat                                                            10

<210> SEQ ID NO 29
<211> LENGTH: 10
<212> TYPE: DNA
<213> ORGANISM: Hansenula polymorpha
<220> FEATURE:
<223> OTHER INFORMATION: Description of the sequence: idealised
      TPS1-Promoter segment

<400> SEQUENCE: 29
atgacgtcat                                                            10

<210> SEQ ID NO 30
<211> LENGTH: 10
<212> TYPE: DNA
<213> ORGANISM: Hansenula polymorpha
<220> FEATURE:
<223> OTHER INFORMATION: Description of the sequence: idealised
      TPS1-Promoter segment

<400> SEQUENCE: 30
attgcgcaat                                                            10
```